United States Patent
Brown et al.

(10) Patent No.: US 6,239,159 B1
(45) Date of Patent: May 29, 2001

(54) NUCLEOSIDE ANALOGUES

(75) Inventors: Daniel Brown, Cambridge; David Loakes, Herts; Alan Hamilton; Adrian Simmonds, both of Bucks; Clifford Smith, Herts, all of (GB)

(73) Assignee: Amersham Pharmacia Biotech UK Limited, Buckinghamshire (GB)

( * ) Notice: Subject to any disclaimer, the term of this patent is extended or adjusted under 35 U.S.C. 154(b) by 0 days.

(21) Appl. No.: 09/101,978

(22) PCT Filed: Feb. 3, 1997

(86) PCT No.: PCT/GB97/00306

§ 371 Date: May 3, 1999

§ 102(e) Date: May 3, 1999

(87) PCT Pub. No.: WO97/28176

PCT Pub. Date: Aug. 7, 1997

(30) Foreign Application Priority Data

Feb. 1, 1996 (GB) .................................................. 9602028

(51) Int. Cl.[7] .............................. A01N 43/52; C12Q 1/68; C12P 19/34; C07H 19/00

(52) U.S. Cl. .............................. 514/394; 514/395; 435/6; 435/91.1; 435/91.2; 536/22.1; 536/23.1; 536/24.3; 536/24.33; 536/24.32

(58) Field of Search .............................. 435/6, 91.1, 91.2; 536/22.1, 23.1, 24.3, 24.33, 25.32; 514/394, 395

(56) References Cited

FOREIGN PATENT DOCUMENTS

| 0 097 373 | 1/1984 | (EP) | .............................. C07H/21/100 |
|---|---|---|---|
| 1 176 419 | 1/1970 | (GB) | .............................. C07D/99/04 |
| WO 91/01325 | 2/1991 | (WO) | .............................. C07H/19/04 |
| WO 94/06810 | 3/1994 | (WO) | .............................. C07H/5/04 |
| WO 95/15395 | 6/1995 | (WO) | .............................. C12P/19/30 |

OTHER PUBLICATIONS

Loakes et al. "3–Nitropyrrole and 5–nitroindole as universal bases in primers for DNA sequencing and PCR" Nucleic Acids Research, vol. 23, No. 13, pp.2361–2366, (No date), 1995.*
Fontanel et al., "P Labeling of Nonnucleosidic Moieties 5′-Attached to Oligonucleotides," *Analytical Biochemistry*, 214:338–340 (1993).
Baker, J.T. et al., "Synthesis and Properties of Pyrrolin–2–ones", *J. Org. Chem.*, 44:2798–2800 (1979).
Loader et al., "Pyrrole chemistry. XXIII. The cyanation of substituted pyrroles with chlorosulfonyl isocyanate (CSI). New syntheses of pyrrole–3–carbonitriles," *Can. J. Chem.*, 59:2673–2676 (1981).

Hronowski et al., "Synthesis of New Carbocyclic Analogues of 3′–Azido– and 3′–Amino–2′, 3′–dideoxynucleosides," *J. Chem. Soc. Chem., Commun.*, pp. 1547–1548 (1990).
Herdewijn et al., "Synthesis and Anti–HIV Activity of Different Sugar–Modified Pyrimidine and Purine Nucleosides," *J. Med. Chem.*, 31:2040–2048 (1988).
Loakes et al., "5–Nitroindole as an universal base analogue," *Nucleic Acids Research*, 22(20):4039–4043 (1994).
Revankar et al., "Direct Synthesis of Pyrrole Nucleosides by the Stereospecific Sodium Salt Glycosylation Procedure," *Nucleosides and Nucleotides*, 6(1&2):261–264 (1987).

(List continued on next page.)

Primary Examiner—Jezia Riley
(74) Attorney, Agent, or Firm—Marshall, O'Toole, Gerstein, Murray & Borun

(57) ABSTRACT

Nucleoside analogues in which a group M replaces the natural base where M is (1) or (2) or (3), where each of $X^1$, $X^2$ and $X^3$ are C or N, each of $R^6$ and $R^7$ is the same or different and each is H, $NO_2$, CO, $COR^8$, $OR^8$, CN, O, $CON(R^8)_2$, $COOR^8$, $SO_2R^8$, $SO_3R^8$, $SR^8$, NHCHO, $(CH_2)_n(R^8)_2$, halogen, or a reporter moiety, each of $R^8$ and $R^9$ is H or hydrocarbyl or a reporter moiety, and n is 0–4. The analogues are substrates for polymerase and terminal transferase enzymes.

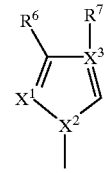

(1)

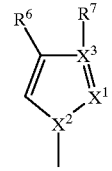

(2)

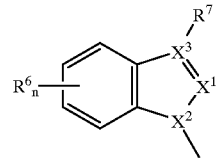

(3)

12 Claims, No Drawings

OTHER PUBLICATIONS

Pochet et al., "Enzymatic Snythesis of 1–(2–Deoxy–β–D–Ribofuranosyl) Imidazole–4–Carboxamide, A Simplified DNA Building Block," *Bioorganic and Medicinal Chemistry Letters*, 5(15):1679–1684 (1995).

Ramasamy, K. et al., "Total synthesis of 2'–deoxytoyocamycin, 2'–deoxysangivamycin and related 7–β–D–arabinofuranosylpyrrolo (2,3–d) pyrimidines via ring closure of pyrrole precursors prepared by the stereospecific sodium salt glycosylation procedure," *Tetrahedron*, 42(21):5869–5878 (1986).

Bergstrom et al., "Design and Synthesis of Heterocyclic Carboxamides as Natural Nucleic Acid Base Mimics," *Nucleosides & Nucleotides*, 15(1–3), 59–68 (1996).

* cited by examiner

NUCLEOSIDE ANALOGUES

Nucleic acids are manipulated in vitro in a wide variety of research and diagnostic techniques. The methods can involve the synthesis of nucleic acid probes by means of polymerase or terminal transferase enzymes for the purposes of labelling or determination of base sequence identity. Labelling often involves the incorporation of a nucleotide which is chemically labelled or which is of a particular chemical composition so as to make it detectable. Nucleic acid probes made in this way can be used to determine the presence of a nucleic acid target which has a complementary sequence by means of hybridisation of the probe to the target.

Another method for introducing chemically labelled or otherwise modified nucleotides into DNA involves chemical synthesis using nucleoside phosphoramidite or other precursors which are linked together in any desired sequence in oligonucleotide synthesisers, the final product being indistinguishable from DNA made by the use of polymerases.

In certain situations it is useful to be able to incorporate a base analogue into an oligo- or poly-nucleotide which does not have the base pairing specificity of the natural bases. Hypoxanthine has been proposed for this purpose in the past because it can form hydrogen bonds with all four natural bases though the strength of binding varies with the different bases. More recently 3-nitropyrrole (WO 94/06810) and 5-nitroindole (Loakes and Brown, Nucleic Acids Research, 1994, 22, 4039–43) have been proposed. They are unlike native bases in their structure, containing only one heteroatom each within the ring structure, nitropyrrole consisting of a single 5-membered ring, and each possessing a nitro grouping as the single exocyclic constituent. Both base analogues have been incorporated into oligonucleotides by chemical synthesis. Melting temperatures (Tm) have been determined for the modified oligonucleotide hybridised to its template. Whilst the Tm for the oligonucleotides was lower when a nitropyrrole or nitroindole was present than when the correct native base was included, the nitroindole and nitropyrrole did not discriminate strongly between different bases at the position opposite within the complementary strand. The synthesis of an imidazole-carboxamide nucleoside monomer for incorporation has also been described (Pochet et al, Bioorganic and Medicinal Chemistry Letters, 5, 1679, (1995)).

The present invention provides a nucleoside analogue of the formula:

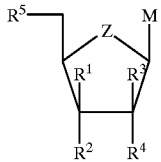

where Z is O, S, Se, SO, $NR^9$ or $CH_2$, $R^1$, $R^2$, $R^3$ and $R^4$ are the same or different and each is H, OH, F, $NH_2$, $N_3$, O-hydrocarbyl or a reporter moiety, $R^5$ is OH or mono, di- or tri-phosphate or -thiophosphate, or corresponding boranophosphate, or one of $R^2$ and $R^5$ is a phosphoramidite or other group for incorporation in a polynucleotide chain, and M is:

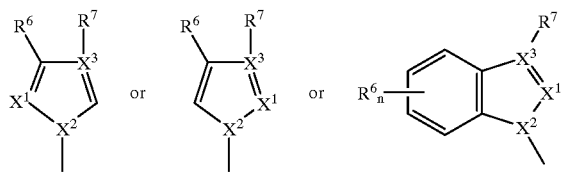

where $X^1$, $X^2$ and $X^3$ are the same or different and each is C or N, when $X^3$ is N then there is no $R^7$ group, $R^6$ and $R^7$ are the same or different and each is H, $NO_2$, CO, $COR^8$, $OR^8$, CN, O, $CON(R^8)_2$, $COOR^8$, $SO_2R^8$, $SO_3R^8$, $SR^8$, NHCHO, $(CH_2)_nN(R^8)_2$, halogen, or a reporter moiety, each of $R^8$ and $R^9$ is H or hydrocarbyl or a reporter moiety, and n is 0, 1, 2, 3 or 4, provided that when $R^5$ is not triphosphate, then the nucleoside analogue comprises a reporter moiety.

A nucleoside analogue is a compound which is capable of being incorporated, by enzymatic or chemical means, in a nucleic acid (DNA or RNA) chain, and is there capable of base-pairing with a nucleotide residue in a complementary chain or base stacking in the appropriate nucleic acid chain. A nucleoside analogue may be specific, by pairing with only one complementary nucleotide; or degenerate, by base pairing with two or three of the natural bases, e.g. with pyrimidines (T/C) or purines (A/G); or universal, by pairing with each of the natural bases without discrimination.

M is a moiety hereafter called a base analogue which may be, but is not necessarily, a base. For example, M may comprise a pyrrole or an indole ring structure.

In one preferred aspect of the invention, the group $R^5$ is triphosphate. When this is the case, the nucleoside triphosphate analogues of the invention are capable of being incorporated by enzymatic means into nucleic acid chains.

In another preferred aspect, the nucleoside analogue of the invention contains a reporter moiety. A reporter moiety may be any one of various things. It may be a radioisotope by means of which the nucleoside analogue is rendered easily detectable, for example 32-P or 33-P or 35-S incorporated in a phosphate or thiophosphate or phosphoramidite or H-phosphonate group, or alternatively 3-H or 125-I. It may be a stable isotope detectable by mass spectrometry. It may be a signal moiety e.g. an enzyme, hapten, fluorophore, chemiluminescent group, Raman label or electrochemical label. The reporter moiety may comprise a signal moiety and a linker group joining it to the remainder of the molecule, which linker group may be a chain of up to 30 carbon, nitrogen, oxygen and sulphur atoms, rigid or flexible, unsaturated or saturated as well known in the field. The reporter moiety may comprise a solid surface and a linker group joining it to the rest of the molecule. The reporter moiety may consist of a linker group with a terminal or other reactive group, e.g. $NH_2$, OH, COOH, $CONH_2$ or SH, by which a signal moiety and/or solid surface may be attached, before or after incorporation of the nucleoside analogue in a nucleic acid chain.

Purine and pyrimidine nucleoside analogues labelled with reporter moieties are well known and well described in the literature. Labelled nucleoside analogues have the advantage of being readily detectable during sequencing or other nucleic acid manipulations.

In the moiety M, $X^1$ and $X^3$ are preferably C and $X^2$ is preferably N. Examples of preferred moieties M are:

(i)

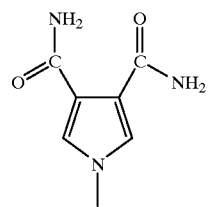

(ii)

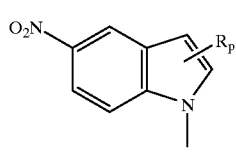

(iii)

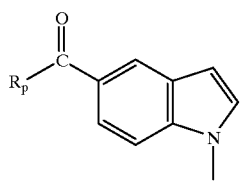

(iv)

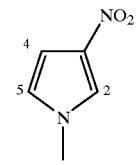

(v)

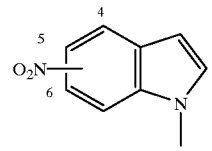

In (i), pyrrole dicarboxamide, either carboxamide group could act as a linkage to a signal moiety or could be replaced by a reporter moiety. In (ii) and (iii), Rp designates a reporter moiety. In (iv), a reporter moiety may also be present at the 2, 4 or 5 position. In (v) a nitro group is present at the 4, 5 or 6 position, and a reporter moiety may also be present. Other examples of M are:

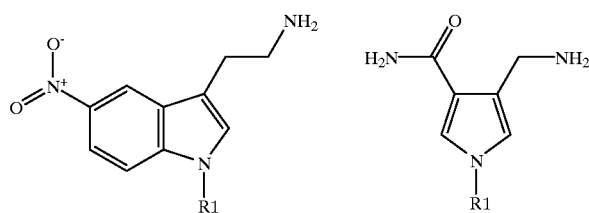

3-aminoethyl-5-nitroindole    3-aminomethyl-4-carboxamido pyrrole

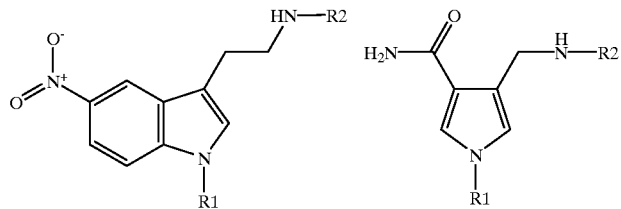

R1 = sugar triphosphate or sugar phosphoramidite
R2 = reporter/substituent

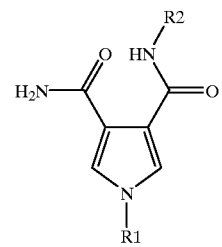

$R^1$, $R^2$, $R^3$ and $R^4$ may each be H, OH, F, $NH_2$, $N_3$, O-alkyl or a reporter moiety. Thus ribonucleosides, and deoxyribonucleosides and dideoxyribonucleosides are envisaged together with other nucleoside analogues. These sugar substituents may contain a reporter moiety in addition to one or two present in the base.

$R^5$ is OH or mono-, di- or tri-phosphate or -thiophosphate or corresponding boranophosphate. Alternatively, one of $R^2$ and $R^5$ may be a phosphoramidite or H-phosphonate or methylphosphonate or phosphorothioate, or an appropriate linkage to a solid surface e.g. hemisuccinate controlled pore glass, or other group for incorporation, hemisuccinate controlled pore glass, or other group for incorporation, generally by chemical means, in a polynucleotide chain. The use of phosphoramidites and related derivatives in synthesising oligonucleotides is well known and described in the literature.

Preferably the moiety M contains a reporter moiety. When a reporter moiety is present, $R^5$ is preferably triphosphate, or alternatively one of $R^2$ and $R^5$ is preferably a phosphoramidite residue. Alternatively when a reporter moiety is not present, the moiety M may itself be detectable, e.g. by binding an antibody or other specific binding reagent which carries an enzyme or fluorescent group.

In the new nucleoside analogues to which this invention is directed, at least one reporter moiety is preferably present in the base analogue or in the sugar moiety or a phosphate group. Reporter moieties may be introduced into the sugar moiety of a nucleoside analogue by literature methods (e.g. J. Chem. Soc. Chem. Commun. 1990, 1547–8; J. Med. Chem., 1988, 31. 2040–8). Reporters in the form of isotopic labels may be introduced into phosphate groups by literature methods (Analytical Biochemistry, 214, 338–340, 1993; WO 95/15395).

The nucleoside analogues of this invention are useful for labelling DNA or RNA or for incorporating in oligonucleotides, with the possible advantage over conventional hapten labelled nucleotides such as fluorescein-dUTP of being able to replace more than one base. A reporter moiety is attached at a position where it does not have a significant detrimental effect on the physical or biochemical properties of the nucleoside analogue, in particular its ability to be incorporated in single stranded or double stranded nucleic acid.

A template containing the incorporated nucleoside analogue of this invention may be suitable for copying in nucleic acid synthesis. If a reporter moiety of the incorporated nucleoside analogue consists of a linker group, then a signal moiety can be introduced into the incorporated nucleoside analogue by being attached through a terminal or other reactive group of the linker group.

A nucleoside analogue triphosphate of this invention may be incorporated by enzymes such as terminal transferase to extend the 3' end of nucleic acid chains in a non-template directed manner.

In primer walking sequencing, a primer/template complex is extended with a polymerase and chain terminated to generate a nested set of fragments where the sequence is read after electrophoresis and detection (radioactive or fluorescent). A second primer is then synthesised using the sequence information near to the end of the sequence obtained from the first primer. This second ("walking") primer is then used for sequencing the same template. Primer walking sequencing is more efficient in terms of generating less redundant sequence information than the alternative "shot gun" approach.

The main disadvantage with primer walking is the need to synthesise a walking primer after each round of sequencing. Cycle sequencing requires primers that have annealing temperatures near to the optimal temperature for the polymerase used for the cycle sequencing. Primers between 18 and 24 residues long are generally used for cycle sequencing. The size of a presynthesised walking primer set required has made primer walking cycle sequencing an impractical proposition. The use of nucleoside analogues that are degenerate or universal addresses this problem. The use of such analogues that are also labelled, e.g. the nucleoside analogues of this invention will also help to overcome the problem. Preferred reporters for this purpose are radioactive isotopes or fluorescent groups, such as are used in conventional cycle sequencing reactions. Where the nucleoside analogues are base specific chain terminators they may be used in chain terminating sequencing protocols.

The nucleoside analogues of this invention can also be used in any of the existing applications which use native nucleic acid probes labelled with haptens, fluorophores or other reporter groups, for example on Southern blots, dot blots and in polyacrylamide or agarose gel based methods. The probes may be detected with antibodies targeted either against haptens which are attached to the base analogues or against the base analogues themselves which would be advantageous in avoiding additional chemical modification. Antibodies used in this way are normally labelled with a detectable group such as a fluorophore or an enzyme. Fluorescent detection may also be used if the base analogue itself is fluorescent or if there is a fluorophore attached to the nucleoside analogue.

The nucleoside analogues of the present invention with the combination of molecular diversity and increased numbers of positions where reporter groups may be added can result in a series of improved enzyme substrates.

EXAMPLE 1

Synthesis of 1-(2'-deoxy-β-D-ribofuranosyl)-5-nitroindole 5'-triphosphate and Phosphorylation of Nucleosides To a stirred solution of 5-nitroindole-2'deoxynucleoside (400 mg, 1.5 mmol) (prepared as described in Loakes, D. and Brown, D. M. (1994) Nucleic Acids Res 22, 4039–4043) in a mixture of triethyl phosphate and trimethyl phosphate (10 ml, 1:1) was added $POCl_3$ (0.6 ml, 6 mmol) dropwise at 0–4° C. The mixture was stirred for 15 hour at 0–4° C. The reaction mixture was then treated with tri-n-butyl ammonium pyrophosphate (7.5 mmol) in anhydrous DMF (20 ml of 0.5M solution) with simultaneous addition of tri-n-butyl amine (7.5 mmol, 1.8 ml). After 10 minutes, the reaction mixture was quenched with 1 M triethylammonium bicarbonate, TEAB (100 ml, pH 7.5) and stirred for 2 hour at room temperature. The crude mixture was purified on Sephadex A-25 column using a linear gradient from 0 to 1 M TEAB (pH 7.5). The triphosphate peak fractions were collected (0.7–0.9 M), concentrated in vacuo and finally purified by reverse phase HPLC.

The nucleosides of 5-formamidoindole, 3-nitropyrrole, pyrrole 3-carboxamide and pyrrole 3,4-dicarboxamide were phosphorylated by analogous methods. The formation of triphosphate products was verified by 31P NMR. Representative $^{31}P$ NMR ($D_2O$) data: −10.28 (d), −10.72 (d) and −22.67 (t).

EXAMPLE 2

Synthesis of 1-(2'-deoxy-β-D-ribofuranosyl)-5-formamidoindole

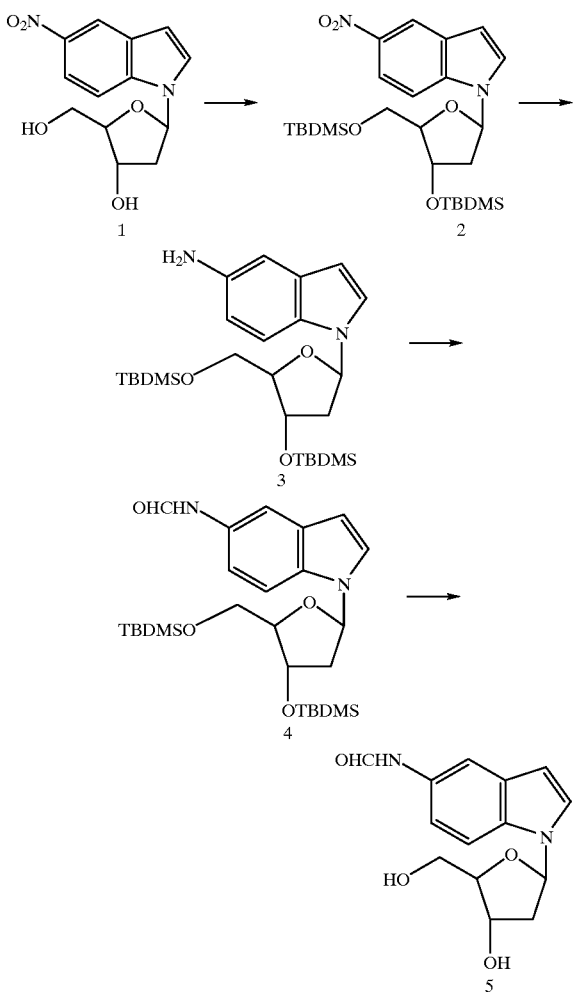

1-(2'-Deoxy-β-D-erythro-pentafuranosyl)-5-nitroindole (1).

The di-O-p-toluoyl nucleoside (Loakes, D. and Brown, D. M., Nucl. Acids Res., 1994, 22, 4039–4043) (3.5 g, 6.8 mmol) was suspended in 80 ml methanolic ammonia and stirred at 45° C. overnight. The solvent was evaporated and the product chromatographed (CHCl$_3$/5% MeOH) to give a yellow foam, (1.81 g, 96%). $^1$H-n.m.r. (DMSO-d6) δ (ppm) 2.25–2.34 (1H, m, H2'), 2.45–2.59 (1H, m, H2'), 3.52–3.62 (2H, m, H5', H5"), 3.83–3.88 (1H, m, H4'), 4.34–4.41 (1H, m, H3'), 4.95 (1H, t, 5'-OH), 5.33 (1H, d, 3'-OH), 6.81 (1H, t, J=6.7 Hz, H1'), 6.81 (1H, d, J=3.3 Hz, H3), 7.82 (1H, d, J=9.2 Hz, H7), 7.88 (1H, d, J=3.3 Hz, H2), 8.03 (1H, dd, J$_1$=9.1 Hz, J$_2$=2.2 Hz, H6), 8.57 (1H, d, J=2.1 Hz, H4). u.v. λmax (nm) 266 (ε=18300), 328.5 (ε=9200), λmin 227.5, 290. ε$_{260}$ (μM)=18.1.

1-(3,5-Di-O-$^t$-butyldimethylsilyl-2'-deoxy-β-D-erythro-pentafuranosyl)-5-nitroindole (2).

To the above nucleoside (0.5 g, 1.9 mmol) in pyridine (25 ml) was added tert-butyldimethylsilyl chloride (0.63 g, 4.2 mmol) and the solution stirred at room temperature overnight. The solution was evaporated, extracted (CHCl$_3$/aqueous NaHCO$_3$), dried and chromatographed (CHCl$_3$) to give a pale yellow gum. Yield 0.87 g, 93%. $^1$H-n.m.r. (DMSO-d6) δ (ppm) −0.01, 0.09 (12H, 2xs, Si-Me), 0.85, 0.88 (18H, 2xs, $^t$-butyl), 2.27–2.35, 2.47–2.59 (2H, m, H2', H2"), 3.64–3.76 (2H, m, H5', H5"), 3.84–3.88 (1H, m, H4'), 4.51–4.56 (1H, m, H3'), 6.43 (1H, t, J=6.6 Hz, H1'), 6.78 (1H, d, J=3.4 Hz, H3), 7.75–7.78 (2H, m, H7, H2), 8.0 (1H, dd, J$_1$=2.3 Hz, J$_2$=9.1 Hz, H6) 8.53 (1H, d, J=2.3 Hz, H4).

1-(3,5-Di-O-$^t$-butyldimethylsilyl-2'-deoxy-β-D-erythro-pentafuranosyl)-5-aminoindole (3).

To the nitroindole (0.9 g, 1.8 mmol) in methanol (40 ml) was added Raney nickel (300 mg) in methanol (10 ml) and the solution stirred under a hydrogen atmosphere for 2 hours. The solution was filtered through celite, evaporated and chromatographed (CHCl$_3$) to give an off-white foam/gum. Yield 0.80 g, 92%. $^1$H-n.m.r. (DMSO-d6) δ (ppm) 0.03, 0.04 (12H, 2xs, Si-Me), 0.88, 0.90 (18H, 2xs, $^t$-butyl), 2.13–2.19 2.46–2.53 (2H, m, H2', H2"), 3.65–3.68 (2H, m, H5', H5"), 3.77–3.8 (1H, m, H4'), 4.48–4.51 (3H, m, H3', NH$_2$), 6.16–6.21 (2H, m, H1', H3), 6.51 (1H, dd, J$_1$=2.1 Hz, J$_2$=8.7 Hz, H6), 6.66 (1H, d, J=1.9 Hz, H4), 7.21 (1H, d, J=8.7 Hz, H7), 7.29 (1H, d, J=3.3 Hz, H2).

1-(3,5-Di-O-$^t$-butyldimethylsilyl-2'-deoxy-β-D-erythro-pentafuranosyl)formamidoindole (4).

The amino indole (0.79 g, 1.66 mmol) was heated at reflux with ethyl formate (25 ml) for 5 hours. The solvent was removed and the product chromatographed (CHCl$_3$/1% MeOH) to give an orange gum/foam. Yield 0.72 g, 86%. $^1$H-n.m.r. (DMSO-d6) δ (ppm) 0.001, 0.07 (12H, 2xs, Si-Me), 0.84, 0.87 (18H, 2xs, $^t$-butyl), 2.19–2.21, 2.46–2.54 (2H, m, H2', H2"), 3.63–3.67 (2H, m, H5', H5"), 3.77–3.79 (1H, m, H4'), 4.47–4.96 (1H, m, H3'), 6.42 (1H, d, J=3.2 Hz, H3), 7.23 (1H, d, J=8.7 Hz, H7), 7.46–7.50 (2H, m, H6, H2), 7.86 (1H, s, CHO), 8.19 (1H, s, H4), 9.97 (1H, s, NH).

1-(2'-Deoxy-β-D-erythro-pentafuranosyl)-5-formamidoindole (5).

The silylated nucleoside (0.7 g, 1.4 mmol) in ethanol (25 ml) and ammonium fluoride (0.5 g, 14 mmol) was heated at reflux overnight. The solvent was removed and the product chromatographed (twice, CHCl$_3$/10% MeOH) to give an off-white powder. Yield 200 mg, 52%. $^1$H-n.m.r. (DMSO-d6) δ (ppm) 2.16–2.22 and 2.43–2.45 (2H, m, H2', H2"), 3.43–3.56 (2H, m, H5', H5"), 3.79–3.80 (1H, m, H4'), 4.32–4.33 (1H, m, H3'), 4.84 (1H, t, 5'-OH), 5.24 (1H, d, 3'-OH), 6.31 (1H, t, J=6.6 Hz, H1'), 6.44 (1H, d, J=3.2 Hz, H3), 7.24 (1H, d, J=8.7 Hz, H7), 7.50 (1H, d, J=8.9 Hz, H6), 7.55 (1H, d, J=2.8 Hz, H2), 7.88 (1H, s, CHO), 8.23 (1H, Br. s, H4), 9.96 (1H, s, NH).

EXAMPLE 3

Synthesis of 1-(2'-deoxy-β-D-ribofuranosyl)-5-aminoindole 5'-triphosphate

To an aqueous solution (3 ml) of 1-(2'-deoxy-β-D-ribofuranosyl)-5-nitroindole 5'-triphosphate (10 mg) in a glass Parr hydrogenation pressure vessel was added 10% Pd/C (5 mg) and hydrogenated for 2 h at 30 psi H$_2$. The reaction mixture was filtered through a pad of Celite, the filtrate purification on a delta Pak C18 column (1.9 cm×30 cm), 15 microns, using the gradient of 0–100% buffer A (0.1M TEAB, pH 7.1) and buffer B (25% CH3CN in 0.1M TEAB) at 12 ml/min in 30 minutes to provide the aminoindole nucleoside triphosphate (6 mg). UV (H$_2$O) λmax 269 nm, $^{31}$P NMR (D$_2$O/EDTA) ppm −6.51(d) γ P, −10.46 (d) α P, −21.99 (t) β P

EXAMPLE 4

Synthesis of 1-(2-deoxy-β-D-ribofuranosyl)-3-(2-N-(2,4-dinitrophenylacyl) aminoethyl)indole*

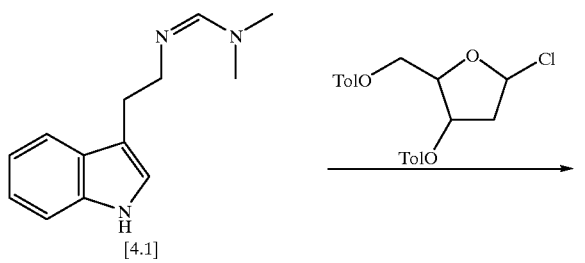

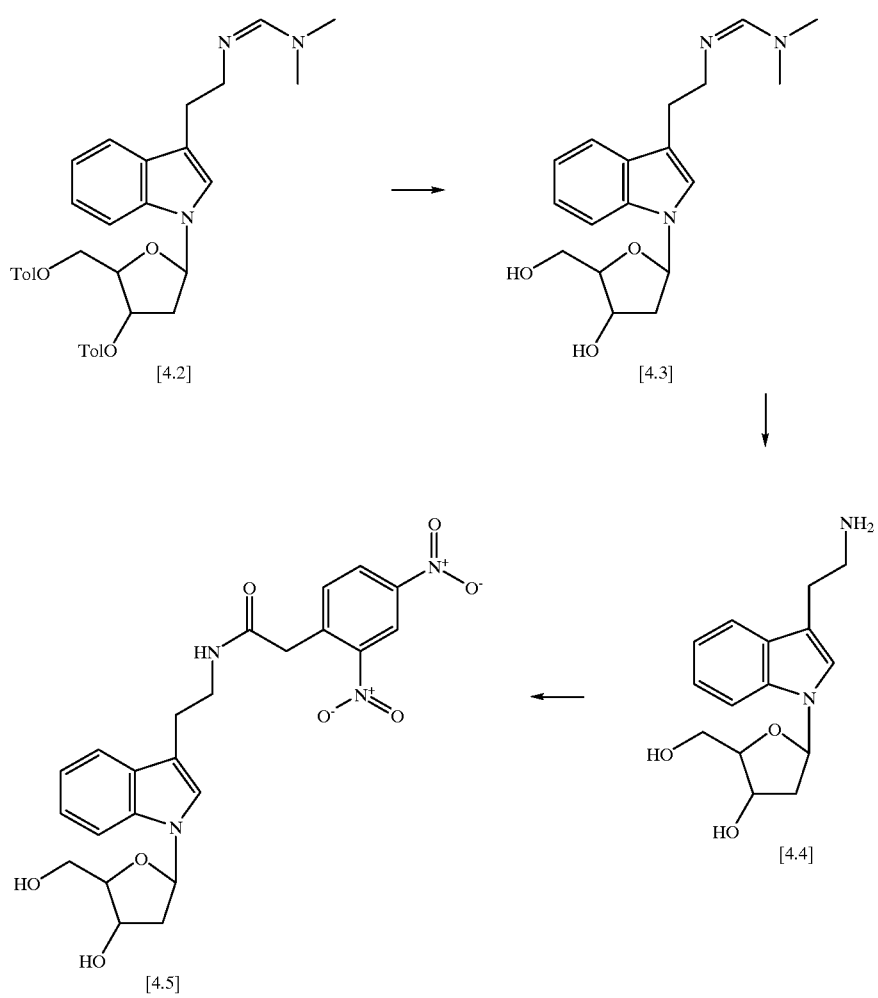

1-(3,5-Di-O-p-toluoyl-2-deoxy-β-D-ribofuranosyl)-3-(2-N-(N',N'-dimethylaminomethylene)aminoethyl)indole (2)*

To a solution of 3-(2-N-(N',N'-dimethylaminomethylene) aminoethylindole (1) (304 mg, 1.41 mmol) in acetonitrile (dry, 8 ml) was added sodium hydride (60% dispersion in oil, 62 mg, 1.54 mmol) and the solution stirred at room temperature for 30 min. α-3,5-Di-O-p-toluoyl-2-deoxyribofuranosyl chloride (657 mg, 1.69 mmol) was added and the solution stirred for 3 hours. The solvent was removed in vacuo and the residue dissolved in chloroform. The title compound was obtained after flash column chromatography (CHCl₃:MeOH, 9:1 gradient to CHCl₃:MeOH, 17:3 ) to give the product. The product was further purified by chromatotron (CH$_2$Cl$_2$:MeOH, 8:1) to give a clear oil (388 mg, 48%). $^1$H-n.m.r. (300 MHz, CDCl$_3$) δ (ppm) 11.00 (1H, m, NCHN), 7.95 (4H, m, Ar), 7.69 (1H, m, Ar), 7.50 (1H, m, Ar), 7.31 (4H, m Ar), 7.16 (2H, m Ar), 6.84 (H, 2×d, H2), 6.46 (1H, m, H1'), 5.75 (1H, m, H3'), 4.82–4.49 (3H, m, H4', H5', H5"), 3.68 and 3.24 (2H, m), 3.19, 3.15 (4H, 2×s and m, 2×NCH$_3$), 3.12–2.86 (2H, m), 2.74–2.71 (4H, 2×s and m, 2×NCH$_3$), 2.48, 2.46, 2.45 (6H, 3×s, ArCH$_3$); MS (ES+) requires 567 (found M+1+, 568, 100%).

1-(2-Deoxy-β-D-ribofuranosy)-3-(2-N-(N', N'dimethylaminomethylene)aminoethyl)indole (3)*

1-(3,5-Di-O-p-toluoyl-2-deoxy-β-D-ribofuranosyl)-3-(2-N-(N',N'-dimethylaminomethylene)aminoethyl)indole (2)

(178.9 mg, 0.315 mmol) was dissolved in methanol (dry, 12 ml) and sodium methoxide (17 mg, 0.315 mmol) added. The solution was stirred for 14 h. T.l.c. revealed disappearance of starting material and appearance of a slower running spot (CHCl$_3$:MeOH, 6.5:1). The solution was neutralized with Dowex 50 (H+) ion-exchange resin and filtered and the filtrate evaporated to dryness. The residue was washed with ether (~2×2 ml) to give the product as a white solid (123 mg, 100% crude). $^1$H-n.m.r. (300 MHz, MeOH-d4) δ (ppm) 8–7 (m, Ar and NCHN), 6.43 (1H, dd, J=6.00, 7.84 Hz, H1'), 4.51 (1H, m, H3'), 3.97 (1H, m, H4'), 3.72 (2H, m, H5', H5"), 3.59 (2H, t, J=6.83 Hz, CH$_2$CH$_2$), 3.02 (2H, t, J=6.87 Hz, CH$_2$CH$_2$), 2.91 (6H, s, N(CH$_3$)2, 2.60 (1H, m, H2'), 2.34 (2H, m, H2").

1-(2-Deoxy-β-D-ribofuranosyl)-3-(2-N-aminoethyl)indole (4)*

1-(2-Deoxy-β-D-ribofuranosyl)-3-(2-N-(N',N'-dimethylaminomethylene)aminoethyl)indole (3) (123 mg) was dissolved in saturated NH$_3$ in methanol (14 ml) and NH$_3$ (aq) (2 ml) and the solution stirred overnight (~14 h). A slower running spot was detected by tlc (CHCl$_3$:MeOH, 4:1). The solvent was removed in vacuo and water removed on a freeze dryer. The crude product was adsorbed onto silica gel from methanol and subjected to flash chromatography (CHCl$_3$:MeOH, 4:1-CHCl$_3$:MeOH, 2:1) with a NH$_3$ (aq) (~10 drops per 250 ml) added. The product was obtained (42.8 mg, 49%) as a solid. $^1$H (300 MHz, MeOH-d4) δ (ppm) 7.55 (3H, m, Ar), 7.28–7.13 (2H, m, Ar), 6.44 (1H, m, H1'), 4.50 (1H, m, H3'), 3.97 (1H, m, H4'), 3.71 (2H, m, H5', H5"), 3.24 (2H, m, CH$_2$CH$_2$), 3.14 (2H, m, CH$_2$CH$_2$), 2.63 (1H, m, H2'). 2.34 (1H, ddd, J=3.13, 5.99, 13.55 Hz, H2").

1-(2-deoxy-β-D-ribofuranosyl)-3-(2-N-(2,4-dinitrophenylacyl)aminoethyl)indole (5)*

To 1-(2-deoxy-β-D-ribofuranosyl)-3-(2-aminoethyl) indole (43 mg, 0.16 mmol) in anhydrous DMF (4 ml) was added the N-hydroxysuccinimidyl ester of 2,4-dinitrophenylacetic acid (100 mg, 0.31 mmol) and anhydrous triethylamine (50 µl, 0.36 mmol) and the reaction left to stir at room temperature under nitrogen for 1 hour. T.l.c. analysis (chloroform/methanol; 9:1) still indicated the presence of the starting amine. The reaction was driven to completion by the addition of further quantities of the N-hydroxysuccinimidyl ester of 2,4-dinitrophenylacetic acid (100 mg, 0.31 mmol) triethylamine (100 µl, 0.72 mmol) and stirring for a further 1 hour at room temperature. The reaction solvent was removed by exhaustive coevaporation with toluene to provide a reddish gum. The product was purified by repetitive flash chromatography (chloroform/methanol, 9:1) to give the title compound as a red gum contaminated with some 2,4-dinitrophenylacetic acid. Yield 24 mg. Rf 0.35 (chloroform/methanol, 9:1)

$^1$H (300 MHz; CD$_3$OD) δ (ppm) 2.2 (1H, m, sugar H2), 2.4 (1H, m, sugar H2), 3.9 (2H, t, =C—CH$_2$), 3.4–3.5 (2H,m, CH$_2$—NHCO), 3.55–3.7 (2H,m,sugar 2-H5), 3.9 (1H,m,sugar H4), 4.05 (2H, s, NHC(O)CH$_2$), 4.45 (1H, m, sugar H3), 6.4 (1H, m, sugar H1), 7.0–7.5 (5H, m, ArH, indole H2), 7.7 (1H, m, DNP-ArH), 8.4 (2H, m, DNP-ArH), 8.8 (2H, m, DNP-ArH). Also present, signals from 2,4-dinitrophenylacetic acid: 3.9 (m, CH$_2$), 7.55 (m, DNP-ArH), 8.35 (m, DNP-ArH), 8.8 (m, DNP-ArH).

*Some α anomer was also present which was difficult to separate by chromatography.

EXAMPLE 5

Synthesis of 1-(2'-deoxy-β-D-ribofuranosyl)-pyrrole-3-carboxamide

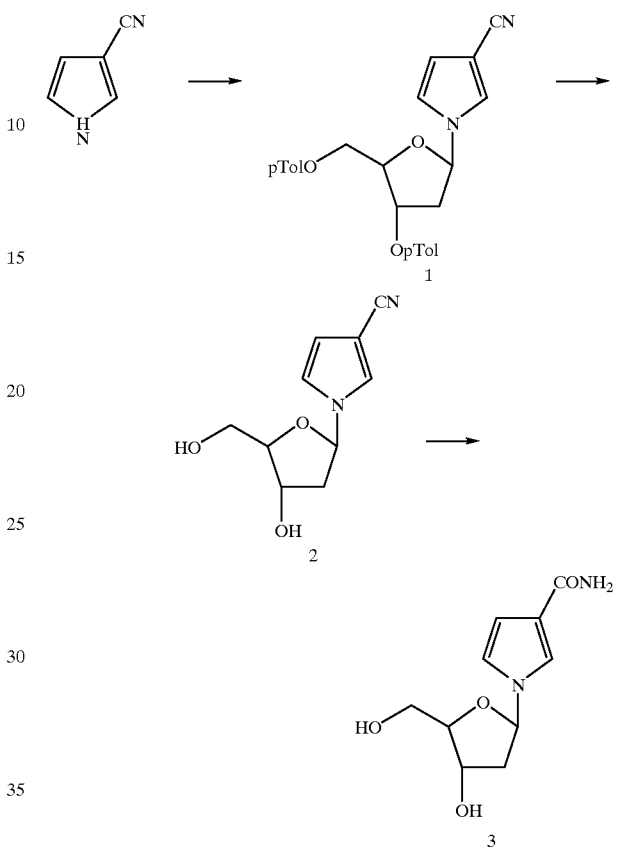

1-(3',5'-Di-O-p-toluoyl-2'-deoxy-β-D-ribofuranosyl)-3-cyanopyrrole, (1).

3-Cyanopyrrole (Can. J. Chem., 1981, 59, 2673) (0.77 g, 8.4 mmol) was dissolved in dry acetonitrile (25 ml) and sodium hydride (60%, 0.38 g, 9.5 mmol) and the solution stirred at room temperature for 30 minutes. To this was then added 1-(3,5-di-O-p-toluoyl-2'-deoxyribofuranosyl) chloride (3.4 g, 10 mmol) and the solution stirred at room temperature for 2 hours. The solvent was removed and the product chromatographed (CHCl$_3$) and then recrystallised from methanol to give an off-white solid. Yield 2.06 g (second crop yielded a further 1.18 g, total yield 87%). $^1$H-n.m.r. (DMSO-d6) δ (ppm) 2.37. 2.39 (6H. 2×s. 2×PhCH$_3$), 2.69–2.81 (2H, m, H2', H2"), 4.48–4.59 (3H, m, H5', H5", H3'), 5.62–5.63 (1H, m, H4'), 6.20 (1H, t, J=6.2 Hz, H1'), 6.51 (1H, d, J=2 Hz, H5), 7.17 (1H, d, J=2 Hz, H4), 7.31–7.37, 7.84–7.94 (9H, m, H2, Ph). FAB mass, 445.3 (M+H)$^+$.

1-(2'-deoxy-β-D-ribofuranosyl)-3-cyanopyrrole, (2).

The above nucleoside (3.2 g, 7.2 mmol) was heated at reflux in 10% triethylamine in methanol (25 ml) for 12 hours. The solvent was evaporated and the product chromatographed (CHCl$_3$/5% MeOH) to give a clear gum. Yield 1.02 g (70%). $^1$H-n.m.r. (DMSO-d6) δ (ppm) 2.16–2.34 (2H, m, H2', H2"), 3.40–3.49 (2H, m, H5', H5"), 3.77–3.81 (1H, m, H4'), 4.28 (1H, Br. s, H3'), 4.97 (1H, s, OH), 5.24 (1H, s, OH), 5.95 (1H, t, J=6.4 Hz, H1'), 6.47 (1H, d, J=2 Hz, H5), 7.15 (1H, d, J=2 Hz, H4), 7.82 (1H, s, H2).

1-(2'-deoxy-β-D-ribofuranosyl)-pyrrole-3-carboxamide, (3).

The cyanopyrrole (1 g, 4.4 mmol) was dissolved in methanol (50 ml) and dioxan (5 ml) and the pH adjusted to pH 9 with ammonia solution. Hydrogen peroxide (30%, 5 ml) was then added to the solution which was then stirred at room temperature overnight. The solution was evaporated and chromatographed (CHCl$_3$/20% MeOH) to give a white foam. Yield 0.65 g, 60%. $^1$H-n.m.r. (DMSO-d6) δ (ppm) 2.12–2.31 (2H, m, H2', H2"), 3.38–3.41 (2H, m, H5', H5"), 3.74–3.78 (1H, m, H4'), 4.24–4.27 (1H, m, H3'), 4.85 (1H, t, 5'-OH), 5.22 (1H, d, 3'-OH), 5.86 (1H, t, J=6.3 Hz, H1'), 6.43 (1H, d, J=2 Hz, H4), 6.70 (1H, NH), 6.94 (1H, d, J=2 Hz, H5), 7.27 (1H, NH), 7.50 (1H, s, H2). u.v. (H$_2$O), λmax. 229 (ε=8000), ε260 (μM)=3.4.

EXAMPLE 6

Synthesis of 1-(2-deoxy-β-D-ribofuranosyl)-4-aminomethyl-pyrrole-3-carboxamide and Linkage to Aminocaproate

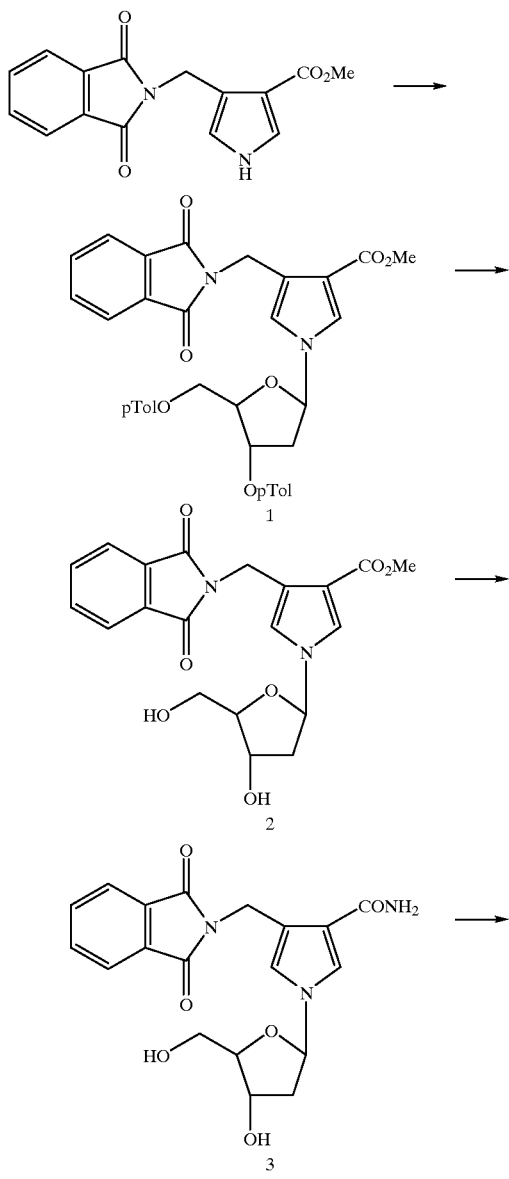

-continued

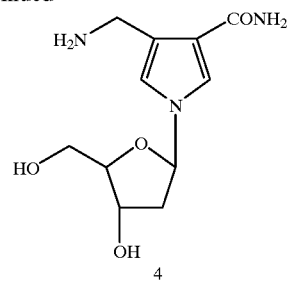

Methyl-1-(3,5-di-O-p-toluoyl-2-deoxy-β-D-ribofuranosyl)-4-phthalimidomethyl-pyrrole-3-carboxylate, (1).

To a solution of the pyrrole (Baker, J. T. and Sifniades, S., J. Org. Chem., 1979, 44, 2798) (1.5 g, 5.3 mmol) in acetonitrile (25 ml) was added sodium hydride (60%, 0.23 g, 5.7 mmol) and the solution stirred at room temperature for 30 minutes. To this was then added the chlorosugar (2.5 g, 6.4 mmol) and the solution stirred overnight. The solvent was removed and the product crystallised from methanol to give a yellow solid. Yield 3.0 g, 90%. $^1$H-n.m.r. (DMSO-d6) δ (ppm) (CDCl$_3$) 2.42 (6H, 2×s, 2×ArCH$_3$), 2.58 (2H, m, H2', H2"), 3.75 (3H, s, OCH$_3$), 4.48 (1H, m, H4'), 4.55 (2H, m, H5', H5"), 5.05 (2H, s, CH$_2$NPhth), 5.58 (1H, m, H3'), 5.90 (1H, t, H1'), 6.88 (1H, s, H5), 7.25 (4H, m, 4×ArCH), 7.50 (1H, s, H2), 7.70–7.90 (4H, m, 4×ArCH), 7.90 (6H, m, ArCH).

Methyl-1-(2-deoxy-β-D-ribofuranosyl)-4-phthalimidomethyl-pyrrole-3-carboxylate, (2).

To a suspension of the above nucleoside (3 g, 4.7 mmol) in methanol (50 ml) was added sodium methoxide (0.55 g, 10 mmol) and the solution stirred at room temperature for 2 hours. The solvent was removed and the product chromatographed (CHCl$_3$/5% MeOH) to give an off-white solid, yield 1.45 g, 77%. $^1$H-n.m.r. (DMSO-d6) δ (ppm) 2.10–2.23 (2H, m, H2', H2"), 3.41 (2H, m, H5', H5"), 3.71 (4H, m, H4', OCH$_3$), 4.19 (1H, m, H3'), 4.81 (2H, s, CH$_2$N), 4.83 (1H, t, 5'-OH), 5.17 (1H, d, 3'-OH), 5.81 (1H, t, H1'), 6.86 (1H, s, H5), 7.64 (1H, s, H2), 7.88 (4H, m, Ar). FAB mass 401.2 (M+H)$^+$.

1-(2-Deoxy-β-D-ribofuranosyl)-4-phthalimidomethyl-pyrrole-3-carboxamide, (3).

The ester (1.4 g, 3.5 mmol) was dissolved in 0.880 ammonia (25 ml) and the solution stirred at room temperature overnight. The solvent was removed and the product chromatographed (CHCl$_3$/20% MeOH) to give a white powder, yield 0.92 g, 68%. $^1$H-n.m.r. (DMSO-d6) δ (ppm) 2.08–2.30 (2H, m, H2', H2"), 3.40–3.49 (2H, m, H5', H5"), 3.69 (2H, s, CH$_2$N), 3.80–3.81 (1H, m, H4'), 4.29 (1H, br. s, OH), 4.37–4.39 (1H, m, H3'), 5.22 (1H, br. s, OH), 5.90 (1H, t, H1'), 7.27–7.59 (6H, m, H2, H5, ArCH), 9.70 (2H, br. s, NH$_2$).

1-(2-Deoxy-β-D-ribofuranosyl)-4-aminomethyl-pyrrole-3-carboxamide, (4).

The phthalimido compound (0.9 g, 2.3 mmol) was dissolved in water (10 ml) and hydrazine hydrate (0.7 ml, 22 mmol) added and the solution heated at reflux overnight. The solvent was removed and the product purified on ion exchange column (Dowex 50WX8-200, H$^+$ form) and eluted with 0.5M ammonia to give a pale brown solid. yield 0.35 g, 56%. $^1$H-n.m.r. (DMSO-d6) δ (ppm) 2.04–2.29 (2H, m, H2', H2"), 3.76 (2H, br. s, CH$_2$N), 3.90–3.94 (1H, m, H4'), 3.35–3.45 (2H, m, H5', H5"), 4.25–4.26 (1H, m, H3'), 4.8–6.6 (6H, br, 2×OH, NH$_2$, CONH$_2$), 5.80 (1H, br. s, H1'), 7.03 (1H, s, H5), 7.51 (1H, s, H2). m/z (+ve EI) 256.1 (M+H)$^+$. u.v. λmax 231.6 (ε=7100). ε260 (μM)=3.2

Linkage of 1-(2-Deoxy-β-D-ribofuranosy)-4-aminomethyl-pyrrole-3-carboxamide to aminocaproate 1-(2-Deoxy-β-D-ribofuranosyl)-4-aminomethyl-pyrrole-3-carboxamide (1 mmol) and the N-hydroxysuccinimidyl ester of N-(trifluoroacetyl)-6-aminohexanoic acid (1.2 mmol) were mixed in carbonate buffer pH 9.2 (20 ml) and stirred at room temperature overnight. The resulting solution was concentrated to dryness and the product was purified by silica gel chromatography using 5–10% methanol/chloroform. $^1$H NMR (DMSO-d6) δ (ppm) 1.32–1.61 (6H, m, 3×CH$_2$), 1.85–2.31 (2H, m, H2', H2"), 3.05 (2H, t, J, 6.8 Hz, NCOCH$_2$), 3.29–3.73 (6H, m, H5', H5", H4', H3', CH$_2$NCOCF$_3$), 4.21 (2H, br s, CH$_2$NHCO), 5.81 (1H, t, J=6.6 Hz, H1'), 6.65 (1H, s, H2), 7.23 (1H, s H5), 8.40, 9.61 (2H, br s×2, NH).

EXAMPLE 7

Synthesis of 1-(2'-deoxy-β-D-ribofuranosyl)-pyrrole-3,4-dicarboxamide

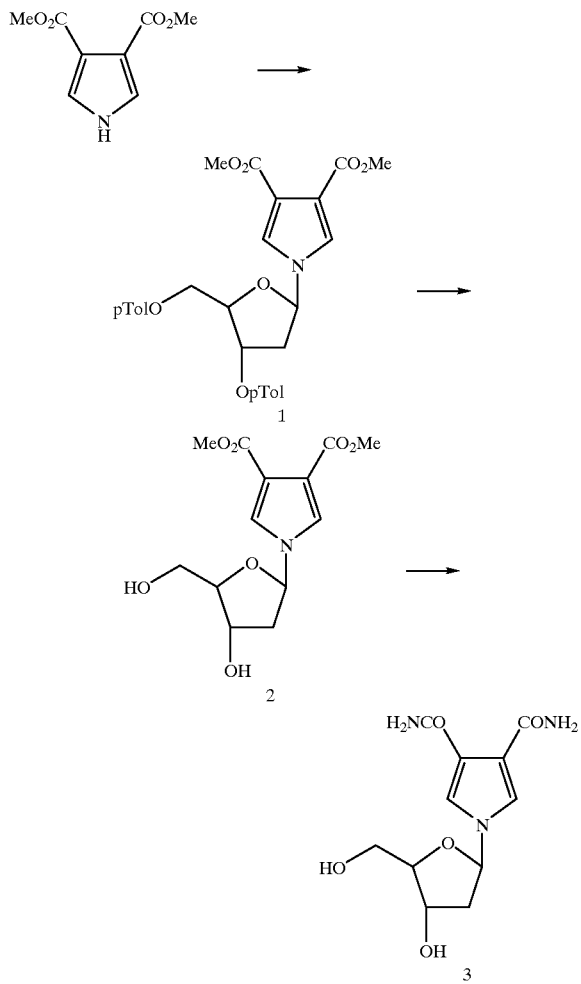

Dimethyl pyrrole-3,4-dicarboxylate.

TOSMIC (1.5 g, 7.7 mmol) was added to a solution of dimethyl fumarate (1 g, 6.9 mmol) and sodium hydride (60%, 0.59, 12.5 mmol) in dry DMF (25 ml) at 0° C., and the solution stirred at 0° C. for 15 minutes. The reaction was poured onto ice-water and the product filtered and recrystallised from aqueous ethanol. 0.61 g, 48%. $^1$H-n.m.r. (DMSO-d6) δ (ppm) 3.68 (6H, s, 2×CH$_3$), 7.39 (2H, s, 2×CH), 11.81 (1H, s, NH).

Dimethyl-1-(3',5'-di-O-p-toluoyl-2'-deoxy-β-D-ribofuranosyl)-pyrrole-3,4-dicarboxylate, (1).

The pyrrole (1 g, 5.5 mmol) was dissolved in acetonitrile (25 ml) and to this was added sodium hydride (60%, 0.25 g, 6.2 mmol) and the solution stirred at room temperature for 30 minutes. To this was then added the chloro sugar (2.5 g, 6.4 mmol) and the solution stirred for 2 hours. The solvent was evaporated and the product worked up as usual and chromatographed (CHCl$_3$/1% MeOH) to give a yellow foam. Yield 1.75 g, 60%. $^1$H -n.m.r. (DMSO-d6) δ (ppm) 2.37, 2.39 (6H, 2×s, 2×ArCH$_3$), 2.71–2.75 (2H, m, H2', H2"), 3.66 (6H, s, 2×OCH$_3$), 4.45–4.60 (3H, m, H3', H5', H5"), 5.61–5.63 (1H, m, H4'), 6.22 (1H, t, J=6.3 Hz, H1'), 7.30–7.37, 7.70–7.94 (8H, m, Ar-H), 7.67 (2H, s, H2, H5).

Dimethyl-1-(2'-deoxy-β-D-ribofuranosyl)-pyrrole-3,4-dicarboxylate, (2).

The di-toluoyl nucleoside (1 g, 1.9 mmol) was suspended in methanol (25 ml) and sodium methoxide (20 mg) added and the solution heated at reflux for 2 hours. The solvent was removed and the product chromatographed (CHCl$_3$/5% MeOH) to give a pale yellow gum. Yield 0.45 g, 81%. $^1$H-n.m.r. (DMSO-d6) δ (ppm) 2.16–2.33 (2H, m, H2', H2"), 3.69 (6H, s, 2×OCH$_3$), 3.51 (2H, br. s, H5', H5"), 3.79–3.83 (1H, m, H3'), 4.26–4.28 (1H, m, H4'), 4.90 (1H, br. s, OH), 5.21 (1H, br. s, OH), 5.96 (1H, t, J=6.4 Hz, H1'), 7.64 (2H, s, H2, H5).

1-(2'-Deoxy-β-D-ribofuranosyl)-pyrrole-3,4-dicarboxamide, (3).

The nucleoside di-ester (0.36 g, 1.2 mmol) was dissolved in 0.880 ammonia solution (10 ml) and heated at 50° C. overnight in a sealed bottle. The solution was cooled and evaporated and the product crystallised from ethanol. Yield 0.26 g, 80%. Spectra as described (Nucleosides & Nucleotides, 1987, 6, 261).

EXAMPLE 8

Synthesis of pyrrole-3,4-dicarboxamide Nucleoside Phosphoramidite

Dimethyl-1-[3-O-(P-b-cyanoethyl-N,N-diisopropylaminophosphinyl)-5-(4,4'-dimethoxytrityl)-2-deoxy-b-D-erythro-pentafuranosyl]-pyrrole-3,4-dicarboxylate.

The nucleoside of dimethylpyrrole-3,4-dicarboxylate (0.45 g, 1.5 mmol) was dissolved in pyridine (25 ml) and to this was added dimthoxytrityl chloride (0.56 g, 1.65 mmol) and the solution stirred at room temperature overnight. The solvent was removed and the product worked up as usual, evaporated and chromatographed (CHCl$_3$/1% MeOH) to give a yellow foam. Yield 0.89 g, 98%. The tritylated nucleoside (1 g, 1.7 mmol) was dissolved in dry dichloromethane (10 ml) under nitrogen and to this was added diisopropylamine (0.86 ml, 4.9 mmol) followed by 2-cyanoethyl diisopropylchlorophosphoramidite (0.56 ml, 2.5 mmol) and the solution stirred at room temperature for 1 hour. To the solution was then added methanol (100 μl) and then the product was dissolved in ethyl acetate (100 ml) and extracted with 10% sodium carbonate (2×25 ml) then saturated brine (2×25 ml), dried and evaporated to dryness. This was then chromatographed (dichloromethane:hexane:triethylamine; 10:10:1) to give the product as a clear gum. Yield 0.71 g, 55%. $^{31}$P-n.m.r. δ (ppm) 147.22, 146.69.

EXAMPLE 9

Primer Extension Assays

Enzyme dependence of 5-nitroindole-2'-deoxynucleoside 5'-triphosphate and 3-nitropyrrole-2'-deoxynucleoside 5'-triphosphate incorporation into DNA For investigations of DNA polymerase activity there was used a primer extension assay using a $^{32}$P or $^{33}$P 5'-end labelled 9 mer primer (5' TGC TGG AGA 3') or 15 mer (5' TGC ATG TGC TGG AGA 3') with a 24 mer template (3' ACG TAC ACG ACC TCT GAT ACA GTC 5', complementary region underlined). Primer (1 pmol) and template (2 pmol) were incubated together in Klenow buffer (50 mM Tris HCl pH 7.5, 5 mM MgCl$_2$ and 5 mM β-mercaptoethanol) at 75° or 90° C. for 2 minutes, then allowed to cool to 30° C. and 10 units 3'-5' exonuclease-free Klenow DNA polymerase added plus 20 μM nucleotides as required. Reactions were incubated at 37° C. for 30 minutes, then a stop solution containing formamide, EDTA and dyes was added. Samples were loaded onto 0.4 mm 18% polyacrylamide denaturing (7M urea) gels and run at about 2 kV for approximately 4 hours. Gels were fixed in 10% methanol/10% acetic acid for 30 minutes and dried onto filter paper. They were then exposed to autoradiography film.

Results with 3'-5' exonuclease-free Klenow, Sequenase™ and ThermoSequenase™ DNA polymerases demonstrated that one dNITP residue could be incorporated into the growing strand. This could indicate the importance of hydrogen bonding of the terminal base for further extension and is in line with other observations which indicate that even with native bases, an incorrect base at the 3' end of a primer precludes further DNA polymerase mediated additions. Results with AMV reverse transcriptase demonstrated that two dNITP residues could be incorporated into the growing chain before further extension was prevented.

Results with dNPTP using exonuclease free Klenow polymerase were similar to those with dNITP though the dNPTP appeared to be a more efficient substrate than dNITP with evidence of the addition of two dNPTP units per primer. However, dNPTP did not appear to be a substrate for AMV reverse transcriptase.

EXAMPLE 10

Template Dependence of Analogue Nucleoside Triphosphate Incorporation into DNA With Exo Minus Klenow Polymerase In order to determine as what base each analogue triphosphate was incorporating, a primer extension reaction was carried out with 4 templates as follows:

3'<u>ACGTACACGACCTCTCTTGATCAG</u> 5'
3'<u>ACGTACACGACCTCTTGGCTAGTC</u> 5'
3'<u>ACGTACACGACCTCTACCTTGCTA</u> 5'
3'<u>ACGTACACGACCTCTGAACTAGTC</u> 5'

Primer complementary to the sequence underlined was 5' end labelled with [γ $^{33}$P] ATP and T4 polynucleotide kinase. Reactions were boiled for 5 minutes after labelling to remove any PNK activity.

For each extension reaction, 1 picomole of $^{33}$P 5'end-labelled primer was hybridised with 2 pmole of template in 10 μl×2 Klenow buffer, though the hybridisation was normally carried out in bulk (e.g. sufficient for 26 reactions) to reduce pipetting errors. The primer and template solution was heated at 75° C. for 3 minutes, then allowed to cool slowly to 30° C. over at least 30 minutes. The solution was diluted twice by the addition of 5 U exonuclease minus Klenow enzyme (Amersham), 2 mU inorganic pyrophosphatase (Amersham) with 40 μM analogue nucleoside triphosphate and/or 4 μM dNTPαS. The choice of dNTPαS was dependent on template sequence. Reactions were incubated at 37° C. for 30 minutes, then stopped by the addition of formamide stop solution. Reaction products were separated on a 19% polyacrylamide 7M urea gel and sized by comparison with a $^{33}$P labelled 8 to 32 base oligonucleotide ladder after exposure to Biomax autoradiography film or a phosphor screen (Storm phosphorimager, Molecular Dynamics).

Single base extensions were seen as expected with the triphosphates of native bases, depending on template sequence and the identity of the base. Addition of the triphosphates of 2 different native bases produced the expected increase in product size and full extension could be obtained in the presence of all four bases. Similarly, chain extension was seen with all of the analogue triphosphates though, once incorporated, not all were able to support further extension, either alone or in the presence of a native base. After a single addition, 5-nitroindole and 3-nitropyrrole were unable to produce further extension on any of the templates and formamidoindole extended very poorly only when incorporated as adenine. The analogues most readily incorporated were pyrrole monocarboxamide and pyrrole dicarboxamide. Both allowed further extension after addition, the monocarboxamide after incorporation as A and T, the dicarboxamide after incorporation as A and C. The results are summarised in the table below:

| Base analogue | Incorporates as: | Extends when incorporated as: |
|---|---|---|
| 5-Nitroindole | A/C/G/T | "terminator" |
| 5-Aminoindole | T > G/C > A | T/G/C** |
| 5-Formamidoindole | A/C/G/T | A* |
| 3-Nitropyrrole | A/C/G/T | "terminator" |
| Pyrrole monocarboxamide | A/T/G/C | A/T*** |
| Pyrrole dicarboxamide | A > C/T/G | A/C**** |

(*****very good; *very poor)

Taq polymerase incorporation of pyrrole mono- and di-carboxamide nucleoside triphosphates into DNA To determine whether Taq polymerase would incorporate the triphosphate of pyrrole monocarboxamide (dMTP) and pyrrole dicarboxamide (dDTP), a primer extension assay was carried out.

The primer (sequence: 5' ACA GGA AAC AGC TAT GAC CA 3') was labelled on the 5' end with $^{33}$P and annealed to a synthetic template (sequence: 5' CTA G <u>TG GTC ATA GCT GTT TCC TGT</u> 3'). In a volume of 18 microliters, containing 10 microliters of 10× Taq polymerase buffer (500 mM KCl, 100 mM Tris pH9 at room temperature, 1% Triton-X 100, 150 mM MgCl$_2$), 12 picomoles of labelled primer was annealed to 60 picomoles of template by heating to 96° C. for three minutes, followed by cooling to room temperature over approximately twenty minutes. Two microliters of Taq polymerase (5 units/microliter) was added, and a series of reactions were set up containing 2 microliters of this primer/template/enzyme mix, made up to 10 microliters with 1 microliter of a 500 μM or 2 mM stock of dMTP or dDTP and 0–4 of the normal dNTPs (final concentration of each: 50 μM) and water. Each ten microliter reaction was covered with paraffin oil before being incubated at 72° C. for one minute. Six microliters of stop solution (95% Formamide, 20 mM EDTA, 0.05%

Bromophenol Blue, 0.05% Xylene Cyanol FF) was added, the reactions were heated to 70° C. for ten minutes, before being loaded on a 0.4 mm thick 12% polyacrylamide/7M urea gel and run at 35 Watts for 150 minutes. Gels were fixed in 10%methanol/12% acetic acid for 15 minutes before being dried onto filter paper and exposed to autoradiography film.

The results are shown in the following table:

| Base analogue | Incorporates as: | Extends when incorporated as: |
| --- | --- | --- |
| Pyrrole dicarboxamide | A and C | A and C |
| Pyrrole monocarboxamide | A, T and C | A and T |

EXAMPLE 11

Oligonucleotide Tailing with Terminal Deoxynucleotidyl Transferase

In order to test the ability of the analogue triphosphates to be accepted by terminal deoxynucleotidyl transferase as a substrate, an oligonucleotide tailing reaction was performed.

A 15 mer primer (sequence: 5' TGC ATG TGC TGG AGA 3') and 8 to 32 base oligonucleotide markers were 5' end labelled with [γ $^{33}$P] ATP and T4 polynucleotide kinase. Reactions were boiled for 5 minutes after labelling to remove any PNK activity. Four picomoles of the labelled primer, 25 U terminal deoxynucleotidyl transferase (TdT) and 32 μM dNTP or analogue triphosphate were incubated in 25 μl 100 mM cacodylate buffer pH7.2, 2 mM $COCl_2$ and 0.2 mM 2-mercaptoethanol for 90 minutes at 37° C. The reactions were stopped by the addition of formamide stop solution and the reaction products run on a 19% polyacrylamide 7M urea gel with the labelled markers. Autoradiography using Biomax film was carried out on the dry gel.

The results showed that the pyrrole-3,4-dicarboxamide triphosphate was an excellent substrate for TdT, the tailing products running at a higher molecular weight than a dATP control. The other analogue triphosphates, though not producing such long reaction products as the pyrrole-3,4-dicarboxamide triphosphate or dATP, also acted as substrates, the product size order being pyrrole-3-monocarboxamide, 3-nitropyrrole, 5-aminoindole and finally 5-nitroindole. The majority of the nitroindole product remained in the sample well, as did much of the nitropyrrole, but this is probably due to the hydrophobic nature of the tails produced in these cases causing aggregation.

EXAMPLE 12

Detection of DNA by Means of Antibodies Directed Against Nitroindole

Antibodies were raised against nitroindole so that DNA containing the nitroindole could be detected. In order to conjugate nitroindole to a protein carrier it was necessary to add a linker and functional group at the 1 position (which is normally occupied by a sugar in the nucleoside).

Synthesis of 1-(4-carboxy butyl)-5-nitroindole

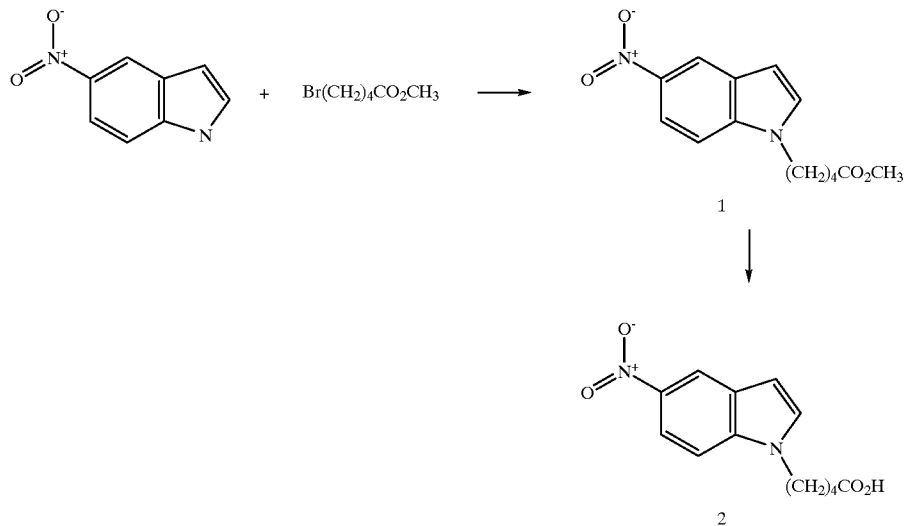

1-(4-methoxycarbonyl butyl)-5-nitroindole (1)

To a stirred solution of 5-nitroindole (0.324 g, 2.0 mmol) in anhydrous acetonitrile (10 ml) was added sodium hydride (0.057 g, 2.38 mmol). The resulting red-brown solution was stirred for 45 minutes, before the addition of a solution of methyl-5-bromovalerate (0.429 g, 2.2 mmol) in anhydrous acetonitrile (1 ml). The solution was stirred for 21 hours, during which time a solid precipitated. Analysis by TLC in chloroform:ethanol (99:1) after 2 hours showed 2 components (starting material: Rf=0.5, 1-(4-methoxycarbonyl butyl)5-nitroindole: Rf=0.8). Further analysis after 21 hours indicated the reaction was essentially complete. The reaction mixture was poured into ethyl acetate (20 ml) and molar HCl (20 ml) and the phases separated. The aqueous phase was extracted with ethyl acetate (20 ml) and the combined organic layer washed with molar sodium bicarbonate solution. The ethyl acetate solution was dried over anhydrous sodium sulphate, filtered and rotary evaporated to give a yellow oil (0.5 g, 1.81 mmol, 91%).

1-(4-carboxybutyl)-5-nitroindole (2)

To 1-(4-methoxy carbonyl butyl)5-nitroindole (0.5 g) was added molar sodium hydroxide (10 ml) and the solution stirred in an oil bath at 120° C. for 90 minutes. It was then cooled, water (10 ml) added and the solution extracted with ethyl acetate (2×15 ml). The combined organic extracts were washed with water (2×10 ml) and the combined aqueous extracts were acidified with molar HCl and extracted with ethyl acetate. (3×15 ml). The organic extracts were dried over anhydrous sodium sulphate, filtered and rotary evaporated to give a yellow gum. The gum was dissolved in hot chloroform, then hexane (2 ml) added and the solution cooled on ice when yellow crystals separated. These were filtered off and washed with chloroform:hexane (50:50) followed by hexane. The crystals were dried in vacuo (0.423 g, 1.61 mmol, 81%), MP 141–2° C. TLC on silica in toluene:methanol:acetic acid (90:16:8) gave one yellow spot and when viewed under UV. Mass spec and NMR analysis were as expected.

Preparation of 1-(4-carboxybutyl)5-nitroindole KLH conjugate

To 1-(4-carboxybutyl)5-nitroindole (19.5 mg, 0.075 mmol) was added anhydrous dimethylformamide (0.5 ml) followed by N-hydroxysuccinimide (11.5 mg, 0.1 mmol) and 1-ethyl-3-(3-dimethyl aminopropyl)carbodiimide (29 mg, 0.15 mmol). This was stirred at room temperature under nitrogen for 90 minutes. Analysis by TLC on silica in toluene:methanol:acetic acid (90:16:8) and chloroform::methanol (98:2) against starting material confirmed the formation of the "active ester", when viewed under UV.

Keyhole limpet hemocyanin (KLH) (45 mg, 0.61 ml) was added to a flask containing water (2.25 ml) and pyridine (0.25 ml). The "active ester" was added dropwise to the above solution with stirring over 5 minutes and then the solution was stirred at room temperature under nitrogen for 4 hours, during which time some flocculent yellow solid separated. The mixture was transferred to a dialysis sac and dialysed against water for 2 nights. The resulting mixture containing some light yellow solid was transferred to a flask and freeze-dried overnight to give 60 mg of final product. This material was submitted to Polyclonal Antibodies Ltd for antiserum production.

Antiserum production

Three sheep were immunised with the KLH conjugate. The primary immunisation was carried out with the conjugate formulated in Freunds complete adjuvant. Subsequent reimmunisations were carried out with the conjugate formulated in Freunds incomplete adjuvant at 4 weekly intervals. Blood samples were taken 2 weeks after each reimmunisation and serum prepared.

Testing of antisera

Antisera were tested against dot blots of nitroindole-labelled oligonucleotides on nylon membrane using a second antibody conjugated to horseradish peroxidase with ECL substrate for detection. The response of pre-immune serum taken from each animal was compared with serum taken from the first and second bleeds.

One microliter aliquots containing 10, 5, 1, 0.5, 0.1, 0.05 and 0.01 pmole of nitroindolelabeled oligonucleotide (sequence: 5' NNN TTC AGC GG 3', where N=5-nitroindole) diluted in water were dotted onto Hybond N+ membrane. A one microliter aliquot of control oligonucleotide (sequence: 5' TGC TGG AGA 3') diluted in water was also applied. Blots prepared in this way were baked at 80° C. for 90 minutes to fix the DNA. After baking, a one microliter aliquot of a 1:1000 dilution of pre-immune serum was dotted onto each blot to give a positive control.

The blots were incubated for 60 minutes at room temperature with shaking in Liquid Block (Amersham) diluted 1:10 with 10 mM phosphate buffered saline (PBS). Individual blots were then incubated for 60 minutes with shaking in 1:1000, 1:10000 or 1:50000 dilutions of each serum sample in 0.5% bovine serum albumin (BSA) solution in PBS. They were then washed 3 times for 10 minutes each wash with shaking in PBS containing 0.3% Tween 20. The blots were then incubated for 60 minutes with shaking in horseradish-peroxidase conjugated affinity-purified donkey anti-sheep IgG, H+L (Jackson ImmunoResearch Labs Inc) diluted 1:25000 in 0.5% BSA in PBS, then washed three times for 10 minutes each wash with shaking in PBS containing 0.3% Tween 20. They were then incubated in ECL detection reagent (Amersham) for 1 to 2 minutes and then exposed to Biomax film (Amersham) for 2 minutes and 5 minutes.

Positive signals were seen from antisera obtained after immunisation of all three sheep at all dilutions but preimmune sera gave a negative response. A maximum sensitivity of 0.1 picomole nitroindole-labelled oligonucleotide was obtained with the 1:1000 antiserum dilution. There was no signal from the unlabelled oligonucleotide but a strong signal was obtained from the positive control.

This experiment demonstrates the potential for detecting or capturing oligonucleotide probes or other probes tailed or otherwise labelled with the nucleotide analogues.

EXAMPLE 13

Pyrrole Analogues

The deoxyriboside of pyrrole-2,3-dicarboxamide is a known compound. The base has been prepared by a different route starting from dimethylfumarate. Reaction with tosylmethylisocyanate (Tosmic) gives the pyrrole dimethylester. Reduction of one of the ester groups gives an alcohol function which can act as a linker for the attachment of a signal group. The nucleoside is prepared by standard procedures, and the ester converted to the amide by treatment with concentrated aqueous ammonia. Having prepared the desired free nucleoside, the phosphoramidite, H-phosphonate and triphosphate derivatives can by synthesised by standard procedures.

EXAMPLE 14

Indole/Indazole Derivatives I

Starting from the indole/indazole base analogue desired a hydroxymethyl group can be introduced onto C-3 by a Mannich type reaction. This base can then be converted to nucleoside/nucleotide derivatives using established procedures. Alternatively, by the same type of general reaction a dimethylaminomethyl group can be introduced onto C-3. This has the advantage that after reaction with methyl iodide to give the quaternary ammonium salt, trimethylamine can be displaced by a carbon or nitrogen or oxygen nucleophile to introduce a longer chain at C-3 to which a reporter group may be attached.

EXAMPLE 15

Indole/Indazole Derivatives II

Starting from the indole/indazole, where R may need to be hydrogen, but could be a suitably protected deoxyribose moiety, radical bromination can occur at C-3 with N-bromosuccinimide. This can then be used in a Heck or related reaction to introduce a variety of linker groups to C-3, such as the allyl alcohol derivative shown to which the reporter groups may be attached. The olefinic bond may have to be reduced. However, if $R^5$ is a nitro group then this will also be reduced. The nitro group, if required, could be introduced after the reduction. Having prepared the desired free nucleoside, the phosphoramidite, H-phosphonate and triphosphate derivatives can be synthesised by standard procedures.

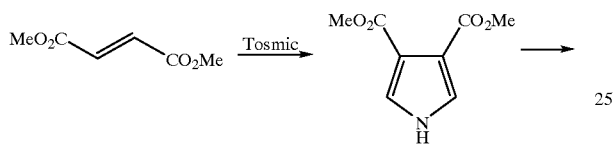

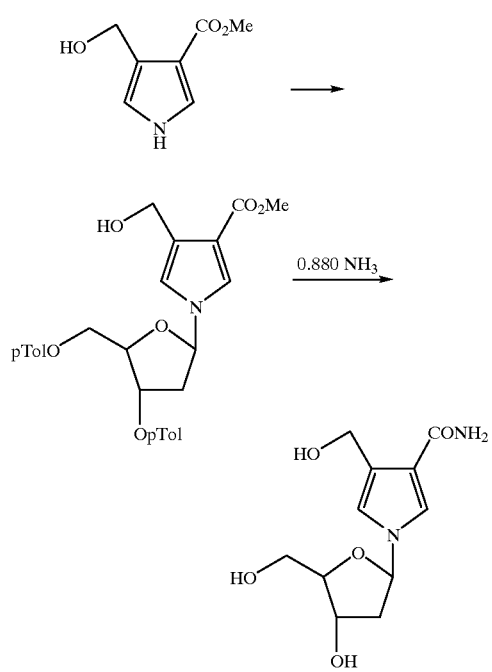

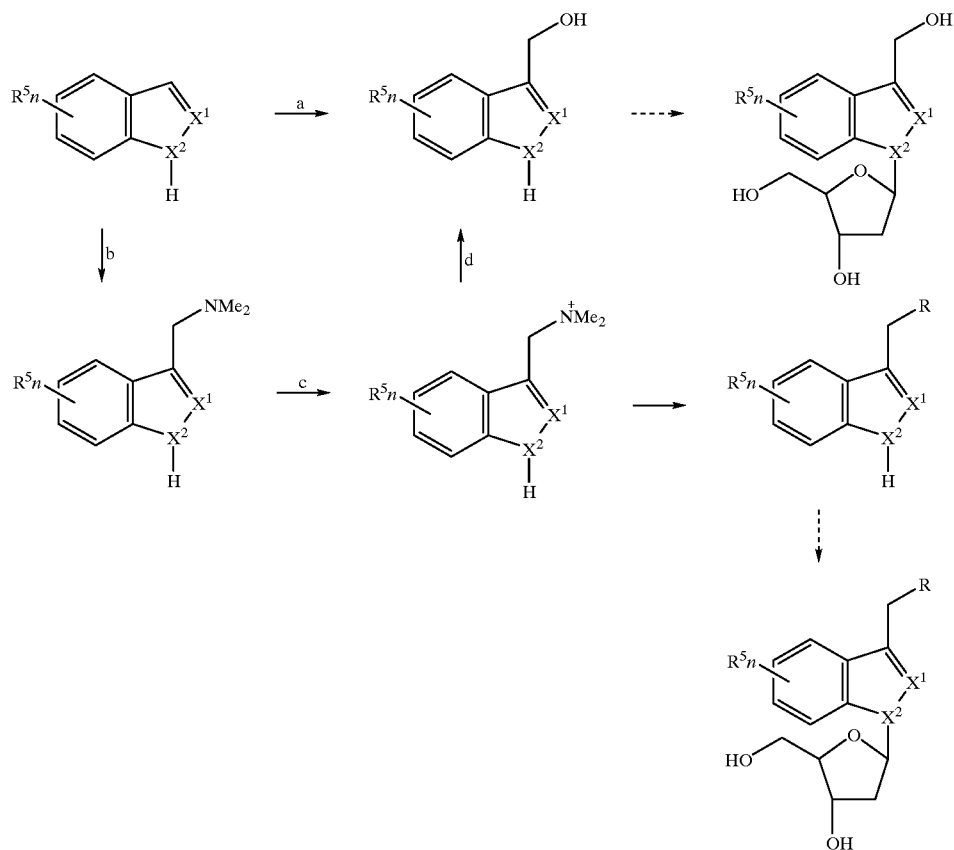

a). Paraformaldehyde/KOH. (b). HCHO/HNMe$_2$
c). MeI. (d). NaOH.

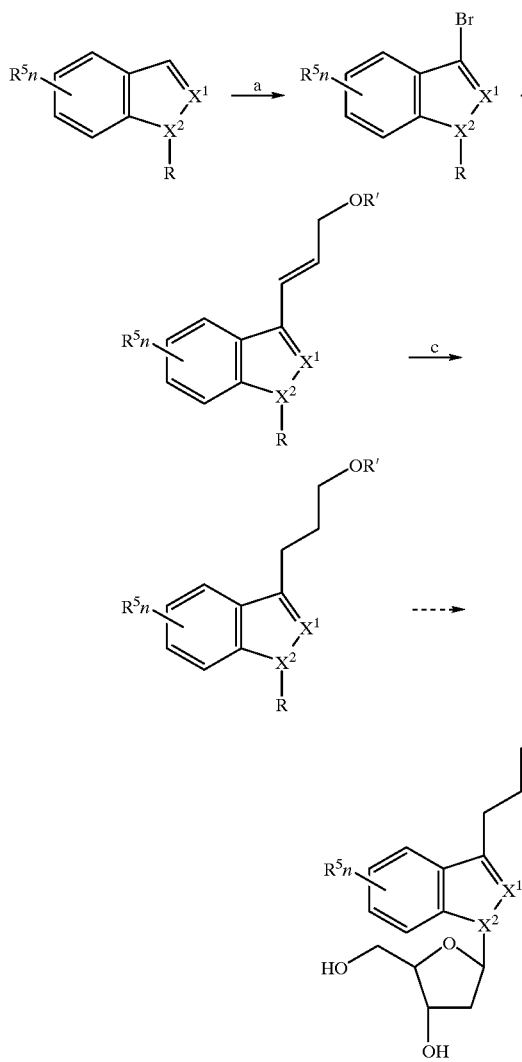

a). N-bromosuccinimide. (b). Pd⁰, CH₂=CHCH₂OR. (c). [H].

What is claimed is:

1. A nucleoside analogue of the formula:

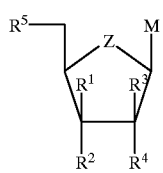

where Z is O, S, Se, SO NR$^9$ or CH$_2$,

R$^1$, R$^2$, R$^3$ and R$^4$ are the same or different and each is H, OH, F, NH$_2$, N$_3$, O-hydrocarbyl or a reporter moiety, R$^5$ is OH or mono-, di- or tri-phosphate or -thiophosphate or corresponding boranophosphate, or one of R$^2$ and R$^5$ is a phosphoramidite or other group for incorporation in a polynucleotide chain, and M is:

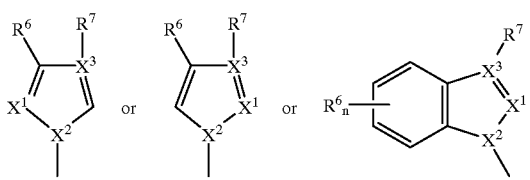

where X$^1$, X$^2$ and X$^3$ are the same or different and each is C or N, when X$^3$ is N, there is no R$^7$ group, R$^6$ and R$^7$ are the same or different and each is H, NO$_2$, CO, COR$^8$, OR$^8$, CN, O, CON(R$^8$)$_2$, COOR$^8$, SO$_2$R$^8$, SO$_3$R$^8$, SR$^8$, NHCHO, (CH$_2$)$_n$N(R$^8$)$_2$, halogen, or a reporter moiety, each of R$^8$ and R$^9$ is H or hydrocarbyl or a reporter moiety, and n is 0, 1, 2, 3 or 4, provided that when R$^5$ is not triphosphate, then the nucleoside analogue comprises a reporter moiety and provided that, when M is benzimidazolyl and a reporter moiety is absent, the M has the structure:

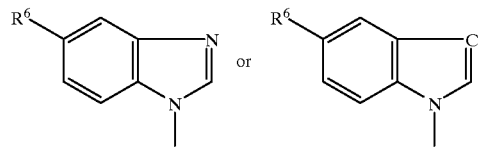

and R$^6$ is not H, and further provided that when M is:

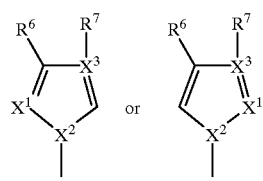

then R$^5$ is not OH.

2. A nucleoside analogue as claimed in claim 1, wherein M contains a reporter moiety.

3. A nucleoside analogue as claimed in claim 1, wherein R$^5$ is triphosphate.

4. A nucleoside analogue as claimed in claim 1, wherein one of R$^2$ and R$^5$ is phosphoramidite or H-phosphonate.

5. A nucleoside analogue as claimed in claim 1, wherein X$^1$ and X$^3$ are C, X$^2$ is N and Z is 0.

6. A nucleoside analogue as claimed in claim 1, wherein the reporter moiety comprises a signal moiety and a linker group.

7. A polynucleotide chain containing at least one residue of a nucleoside analogue according to claim 1.

8. A polynucleotide chain as claimed in claim 7, wherein a signal moiety has been introduced into the incorporated nucleoside analogue residue.

9. A chain extension method which comprises reacting a polynucleotide chain with a nucleoside triphosphate analogue according to claim 1 in the presence of a polymerase.

10. A chain extension method which comprises reacting a polynucleotide chain with a nucleoside triphosphate analogue according to claim 1 in the presence of a terminal deoxynucleotidyl transferase.

11. A method of detecting a nucleic acid which contains a residue of a nucleoside analogue of the formula:

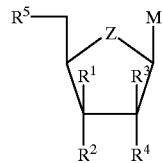

where Z is O, S, Se, SO, $NR^9$ or $CH_2$, $R^1$, $R^2$, $R^3$ and $R^4$ are the same or different and each is H, OH, F, $NH_2$, $N_3$, O-hydrocarbyl or a reporter moiety, $R^5$ is OH or mono-, di- or tri-phosphate or -thiophosphate or corresponding boranophosphate, or one of $R^2$ and $R^5$ is a phosphoramidite or other group for incorporation in a polynucleotide chain, and M is:

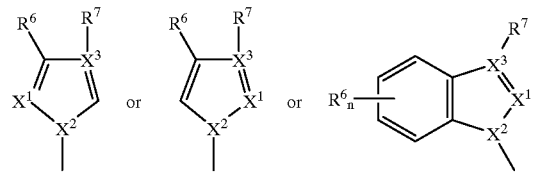

where $X^1$, $X^2$ and $X^3$ are the same or different and each is C or N, when $X^3$ is N, there is no $R^7$ group, $R^6$ and $R^7$ are the same or different and each is H, $NO_2$, CO, $COR^8$, $OR^8$, CN, O, $CON(R^8)_2$, $COOR^8$, $SO_2R^8$, $SO_3R^8$, $SR^8$, NHCHO, $(CH_2)_nN(R^8)_2$, halogen, or a reporter moiety, each of $R^8$ and $R^9$ is H or hydrocarbyl or a reporter moiety, and n is 0, 1, 2, 3 or 4, which method comprises using for detection an antibody which binds to M.

12. [1-(2'-deoxy-β-D-ribofuranosyl)-pyrrole-3,4-dicarboxamide]5'-triphosphate.

* * * * *